United States Patent
Cotton et al.

(10) Patent No.: US 9,616,155 B2
(45) Date of Patent: Apr. 11, 2017

(54) FIXATION DEVICES FOR TISSUE REPAIR

(75) Inventors: Nicholas J. Cotton, Westborough, MA (US); Emma J. Wright, Arlington, MA (US); Steven W. Astorino, Norton, MA (US); Saad Ali, York (GB)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 12/484,274

(22) Filed: Jun. 15, 2009

(65) Prior Publication Data

US 2010/0040662 A1 Feb. 18, 2010

Related U.S. Application Data

(60) Provisional application No. 61/061,317, filed on Jun. 13, 2008.

(51) Int. Cl.
*A61L 31/16* (2006.01)
*A61L 31/04* (2006.01)

(52) U.S. Cl.
CPC ............ *A61L 31/16* (2013.01); *A61L 31/048* (2013.01); *A61L 2300/21* (2013.01); *A61L 2300/414* (2013.01); *A61L 2300/42* (2013.01)

(58) Field of Classification Search
CPC ............................... A61L 31/16; A61L 31/048
See application file for complete search history.

(56) References Cited

U.S. PATENT DOCUMENTS

| | | | |
|---|---|---|---|
| 4,353,996 A | 10/1982 | Marconi et al. | |
| 5,461,139 A | 10/1995 | Gonda et al. | |
| 5,609,629 A * | 3/1997 | Fearnot et al. | 623/1.42 |
| 6,153,252 A * | 11/2000 | Hossainy et al. | 427/2.3 |
| 6,224,630 B1 * | 5/2001 | Bao et al. | 623/17.16 |
| 6,991,804 B2 * | 1/2006 | Helmus et al. | 424/423 |
| 2003/0040809 A1 * | 2/2003 | Goldmann et al. | 623/23.76 |

(Continued)

FOREIGN PATENT DOCUMENTS

| CN | 1826380 | 8/2006 |
|---|---|---|
| CN | 101128225 | 2/2008 |

(Continued)

OTHER PUBLICATIONS

Covidien TI-CRON information brochure, p. 2; www.covidien.com/imageServer.aspx?contentID=14369&contenttype=application/pdf—last accessed Nov. 21, 2011).*

(Continued)

*Primary Examiner* — Cherie M Stanfield
(74) *Attorney, Agent, or Firm* — Norman F. Hainer, Jr.

(57) ABSTRACT

Fixation devices for tissue repair, for example sutures, surgical arrows, staples, darts, bolts, screws, buttons, anchors, nails, rivets, or barbed devices comprise at least one of angiogenic material; angiogenic precursor material which is capable of breaking down in vivo to form angiogenic material; or tissue-engineered material, which tissue-engineered material is capable of producing angiogenic material. In a preferred form, the material is incorporated into a polymer matrix having predetermined hydrophobicity to allow controlled release of angiogenic materials such as butyric or hydroxybutyric acid or salts thereof. Polymer matrix compositions comprising angiogenic materials and methods for tissue repair are also provided.

7 Claims, 7 Drawing Sheets

(56) References Cited

U.S. PATENT DOCUMENTS

| | | |
|---|---|---|
| 2004/0162580 A1 | 8/2004 | Hain |
| 2004/0265282 A1 | 12/2004 | Wright et al. |
| 2005/0277985 A1* | 12/2005 | Wert .............. A61B 17/06166 606/228 |
| 2006/0286289 A1 | 12/2006 | Prajapati et al. |
| 2007/0134292 A1 | 6/2007 | Suokas et al. |

FOREIGN PATENT DOCUMENTS

| | | |
|---|---|---|
| WO | WO 02098475 A1 * | 12/2002 |
| WO | 03105726 | 12/2003 |
| WO | WO2005025449 A2 | 3/2005 |
| WO | WO2006116000 A2 | 11/2006 |

OTHER PUBLICATIONS

Office Action received in corresponding Chinese application No. 200980131831.X mailed Dec. 13, 2013.

Office Action received in corresponding Japanese application No. 2011-513745 mailed Nov. 19, 2013.

Office Action received in corresponding Australian application No. 2009257230 mailed Nov. 29, 2013.

Iso Saito, Industry and Fiber, Fiber Encyclopedia, Maruzen Company, Limited, Seishiro Murata, first edition, p. 108, Mar. 2002.

Office Action received in corresponding Japanese application No. 2011-513745 mailed Mar. 31, 2014.

Office Action for corresponding Chinese Application No. 200980131831.X mailed Mar. 26, 2013.

Duan Xiaojun et al., "Progress and strategy study of facilitating tissue engineering and blood vessel of bone," Chinese Journal of Clinical Rehabilitation, vol. 7 (26), p. 3628-3629, Oct. 2003.

Office Action received in corresponding Japanese patent application No. 2011-513745 mailed Aug. 18, 2014.

Office Action received in corresponding Chinese patent application No. 200980131831.X mailed Jun. 27, 2014.

Office action received for corresponding Chinese patent application No. 200980131831.X mailed Jan. 22, 2015.

Office action received in corresponding Chinese application No. 200980131831.X mailed Jun. 15, 2015, Only portions in English considered.

* cited by examiner

FIXATION DEVICES FOR TISSUE REPAIR

CROSS-REFERENCE TO RELATED APPLICATIONS

This application claims priority to U.S. Patent Application No. 61/061,317 filed on Jun. 13, 2008, the disclosure of which is incorporated herein by reference in its entirety.

BACKGROUND

1. Field of the Invention

The invention is concerned with the provision of fixation devices that improve tissue repair and with the use of such devices in medical treatment. In particular, the invention is concerned with the fixation of tissues, which have limited or no vascular supply, and where angiogenesis is desirable or a prerequisite for good tissue repair.

2. Related Art

A wide variety of fixation devices exist for use in invasive medical treatments. These devices may be used to rejoin, re-affix, hold, or otherwise partake in the repair of tissue during and after surgery and other medical treatments.

An aim of medical practitioners following surgery, for example, is to incite rapid healing and tissue repair throughout the treatment site. A factor in the promotion of tissue repair is the extent to which reparative cells and other factors can permeate through to the tissue in question. This, in turn, is dependent upon the extent to which blood vessels can form in and around the site.

The formation of new blood vessels from pre-existing ones is known as angiogenesis. Angiogenesis is an essential process during development of the human body, particularly embryonic development. Development of the human embryo commences with fusion of blood islands into vascular structures in the process of vasculogenesis; subsequently angiogenesis begins, with new vessels sprouting off from the vessels formed during vasculogenesis. Angiogenesis normally tails off, however, when the body becomes adult. With the exception of the female reproductive system, angiogenesis in the adult mainly occurs during tissue repair after wounding or inflammation, although it is also associated with adult pathological conditions, such as tumor growth, rheumatoid arthritis, psoriasis, and diabetes.

The principle cell type involved in angiogenesis is the microvascular endothelial cell. Following injury and/or in response to angiogenic factors, the basement membrane of endothelial cells in the parent blood vessel is degraded, a process mediated by endothelial cell proteases. Once the basement membrane is degraded, endothelial cells migrate out into the perivascular space. Cells at the base of the sprout proliferate and replace the migrated cells. A new basement membrane is then formed and two contiguous sprouts fuse together to form a loop. Subsequently a lumen forms and blood begins to flow.

The endothelial cell is the central cell type involved in angiogenesis because it is capable of expressing all the necessary information for the formation of new microvascular networks. It appears to achieve this by acting in concert with many different cell types to form new vessels. While not wishing to be bound by any theory, these other cell types may promote angiogenesis by expressing growth factors and cytokines that stimulate the proliferation and migration of the primary cellular components of the vascular wall, including endothelial cells.

Therapeutic angiogenesis is the clinical use of angiogenic factors or, in some cases, genes encoding these factors to enhance or promote the development of blood vessels in ischaemic/avascular tissue. The ideal agent for therapeutic angiogenesis would be safe, effective, inexpensive, and easy to administer. It would also be highly desirable to provide angiogenic factors in a controlled way over a predetermined period of time.

It is an aim of the present invention to provide medical devices, which release angiogenic factors that promote blood vessel formation in the surrounding tissue.

It is a further aim of the present invention to provide fixation devices which promote tissue repair in the surrounding tissue and which will release factors that promote blood vessel vaso-dilation. Delivery of such factors or pharmacological active agents using fixation devices, for example a suture or surgical tape, requires the suture or surgical tape to have certain characteristics to enable it to function as both a suture or surgical tape and a fixation or delivery device. For instance, the suture must have adequate strength, knot tying and sliding properties for it to Junction in its primary role, as a suture. As a biological agent delivery device, the suture must be able to incorporate the active agent within its structure in such a way that the active agent is not changed in any way during the loading. The active agent must be stable within the structure to allow for normal storage prior to use. Once in place in vivo the active agent must be released at a certain dose over a certain time period to maximise its therapeutic properties and minimise adverse reactions. Suture repair, using a standard suture, of certain tissues which have limited or no vascular supply, for example, meniscal cartilage, articular cartilage, ligaments, tendons, bone, and ischaemic tissue can be problematic.

SUMMARY

In one aspect of the invention, the invention relates to a fixation device for tissue repair including at least one of angiogenic material or angiogenic precursor material which is capable of breaking down in vivo to form angiogenic material, wherein the angiogenic material is in admixture with polypropylene.

In an embodiment, the angiogenic material includes one or more of butyric acid, butyric acid salt, α-monobutyrin, α-dibutyrin, β-dibutyrin, tributyrin, or hydroxybutyrate. In another embodiment, the butyric acid salt is selected from sodium, potassium, calcium, ammonium, and lithium salts. In yet another embodiment, the angiogenic material includes one or more of the following angiogenic factors: angiogenic peptide growth factors, including autologous, xenogenic, recombinant, and synthetic forms of these, including the vascular endothelial growth factors VEGF 121, 165, 189 and 206; fibroblast growth factors FGF-1, FGF-2, FGF-7 (keratinocyte growth factor); transforming growth factor family (TGF-α, -β); platelet derived growth factors PDGF-AA, PDGF-BB, and PDGF-AB; platelet derived endothelial cell growth factor (PD-ECGF); hypoxia inducible factor-1 (HIF-1); scatter factor (SF, also known as hepatocyte growth factor or HGF); placenta growth factor (PIGF)-1, -2; tumor necrosis factor α (TNF-α); midkine; pleiotrophin; insulin-like growth factor-1; epidermal growth factor (EGF); endothelial cell growth factor (ECGF); endothelial stimulating angiogenic factor (ESAF); connective tissue growth factor (CTGF); CYR61; Angiogenin; or Angiotrophin.

In a further embodiment, the angiogenic material includes one or more blood clot breakdown products, including thrombin, heparin, and autologous, allogeneic, xenogeneic, recombinant, and synthetic forms of these materials. In yet a further embodiment, the angiogenic material includes one or more of hyaluronan, para-thyroid hormone, angiopoietin 1, del-1, erythropoietin, fas (CD95), follistatin, macrophage migration inhibitory factor, monocyte chemoattractant protein-1, and nicotinamide. In an embodiment, the angiogenic precursor material includes one or more of fibrin, including autologous, allogeneic, xenogeneic, recombinant and synthetic forms thereof, and hyaluronic acid.

In another embodiment, the fixation device is coated on at least one external surface with one or more of the angiogenic material, the angiogenic precursor material, or the tissue-engineered material. In yet another embodiment, the fixation device has at least one of the angiogenic material, the angiogenic precursor material, and the tissue-engineered material impregnated into at least one region thereof. In a further embodiment, the fixation device includes a suture, a surgical arrow, a staple, a dart, a bolt, a screw, a button, an anchor, a nail or rivet, or a barbed surgical device.

In another aspect, the present invention relates to a method of treatment of a mammalian organism in clinical need thereof, including the step of implanting a fixation device into a tissue defect in the mammalian organism, the fixation device including at least one of angiogenic material or angiogenic precursor material which is capable of breaking down in vivo to form angiogenic material, wherein said angiogenic material is in admixture with polypropylene.

In an embodiment, the tissue into which the fixation device is implanted is avascular tissue. In another embodiment, the tissue is meniscal cartilage, articular cartilage, ligament, bone, or ischaemic tissue.

In yet another aspect, the present disclosure relates to a composition of matter. The composition includes a blend of polypropylene and a water-soluble or water miscible angiogenic material or angiogenic precursor in a therapeutically effective amount sufficient to promote angiogenisis. In an embodiment, the angiogenic material includes one or more of butyric acid, hydroxybutyric acid, the sodium, potassium, calcium, ammonium and lithium salts and polymers of said acids, or monobutyrin. In yet another embodiment, the composition contains up to about 12% by weight of the angiogenic material.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE EMBODIMENTS

Figure 1:
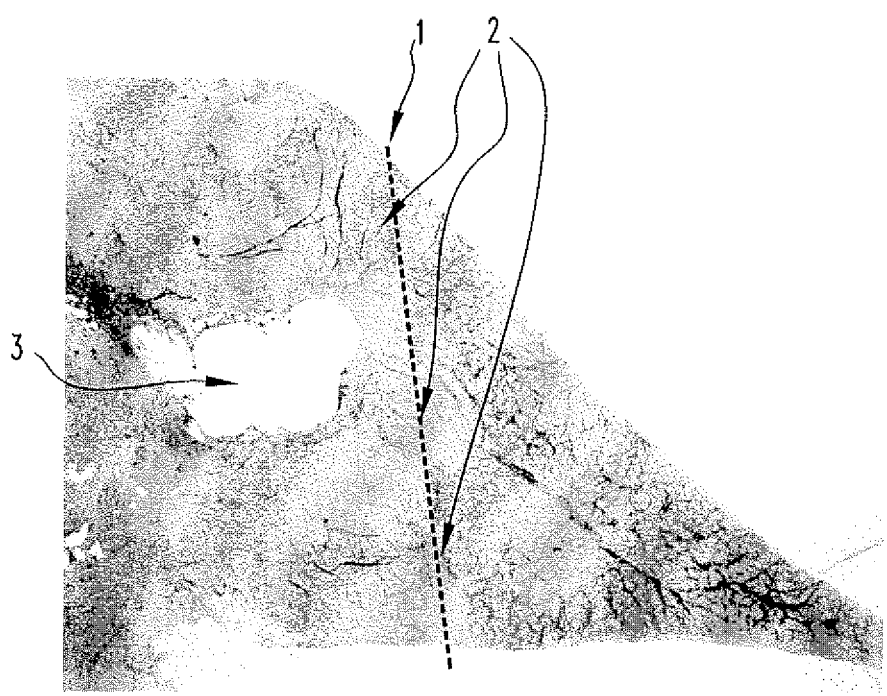
FIG. 1 illustrates a tear in the red-white zone of meniscal cartilage.

As used herein, the term "angiogenic material" is to be understood to include not only material comprising one or more angiogenic factors but also materials which stimulate blood supply by inducing vaso-dilation of pre-existing vascular material.

As used herein, the term "angiogenic factor" is to be understood to include materials, which directly or indirectly promote angiogenesis, for example, materials that are capable of breaking down in vivo to form angiogenic material.

As used herein, the term "angiogenesis" is to be understood to include the growth of new blood vessels from existing ones.

As stated above, the angiogenic material comprises one or more angiogenic factors. A first class of angiogenic factors, which falls within the scope of the invention, comprises angiogenic peptide and protein growth factors, including autologous, allogenic, xenogenic, and recombinant and synthetic forms of these. This class includes the vascular endothelial growth factor family, particularly VEGF 121, 165, 189 and 206; fibroblast growth (actor family, particularly FGF-1, FGF-2, FGF-7 (keratinocyte growth factor); transforming growth factor family (TGF-α, -β);, platelet derived growth factor, particularly PDGF-AA, PDGF-BB and PDGF-AB; platelet derived endothelial cell growth factor (PD-ECGF); hypoxia inducible factor-1 (HIF-1); scatter factor (SF, also known as hepatocyte growth factor or HGF); placenta growth factor (PlGF)-1, -2; tumour necrosis factor-α (TNF-β); midkine; pleiotrophin; insulin-like growth factor-1; epidermal growth factor (EGF); endothelial cell growth factor (ECGF); endothelial stimulating angiogenic factor (ESAF); connective tissue growth factor (CTGF); CYR61; Angiogenin; or Angiotrophin.

A second class of angiogenic factors which falls within the scope of the invention comprises blood clot breakdown products, such as thrombin and heparin including autologous, allogeneic, xenogeneic, and recombinant and synthetic forms of these materials.

A third class of angiogenic factors which falls within the scope of the invention comprises those based around butyric acid, including:

butyric acid (butanoic acid, $C_4H_8O_2$) and butyric acid salts, including sodium, potassium, calcium, ammonium, and lithium salts butyric acid derivatives and polymers containing butyric acid residues α-monobutyrin (1-glycerol butyrate; 1-(2,3 dihydroxypropyl) butanoate; $C_7H_{14}O_4$)

α-dibutyrin (1,3-glyceroldibutyrate; 1,3-(2 hydroxypropyl)dibutanoate; $C_{11}H_{20}O_5$)

β-dibutyrin (1,2-glyceroldibutyrate; 1,2-(3 hydroxypropyl)dibutanoate; $C_{11}H_{20}O_5$)

tributyrin (glycerol tributyrate; 1,2,3-propyl)tributanoate; $C_{15}H_{26}O_6$)

hydroxybutyrate and polymers containing hydroxybutyric acid residues.

The compounds disclosed in PCT International Patent Application Publication WO 90/11075, the disclosure of which is incorporated herein by reference in its entirety, are also expressly included in the scope of the present invention. These have general formula:

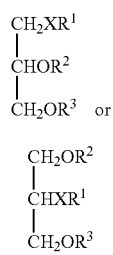

(1)

(2)

wherein X is O, NH, S, or $CH_2$, and $R^1$ is alkyl or acyl of 2-10C which is saturated or unsaturated and which is unsubstituted or substituted with one or more substituents which do not interfere with angiogenic activity, said substituents selected from the group consisting of OH, OR, SH, SR, $NH_2$, NHR, $NR_2$, and halo wherein each R is independently lower alkyl (1-4C); and each $R^2$ and $R^3$ is independently H, $PO_3^{-2}$, or is alkyl or acyl as defined above, or in formula 1, $R^2$, and $R^3$ taken together are an alkylene moiety or $OR^2$ and $OR^3$ form an epoxide, which amount is effective to stimulate angiogenesis in said subject.

wherein $R^2$ and $R^3$ are acyl or H wherein said acyl group is $CH_3(CH_2)_{n1}CO$, wherein n1 is an integer of 0-8; or is neopentoyl or cyclohexylcarbonyl wherein, in the compound of formula 1, $R^2$, and $R^3$ taken together are

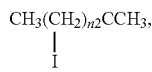

wherein n2 is an integer of 0-7 the method stated above wherein one of $R^2$ and $R^3$ is H and the other is alkyl (1-10C)

the method stated above wherein X is O the method stated above wherein $R^1$ is acyl (2-6C)

A fourth class of angiogenic factors, which falls within the scope of the invention, comprises inflammatory mediators. These materials promote tissue inflammation, which in turn promotes angiogenesis. Included in this class are tumor necrosis factor α (TNF-α); prostaglandins E1 and E2; interleukins 1, 6, and 8; and nitric oxide.

Disparate other angiogenic factors are known which do not fall into any class. Included in this group are hyaluronan, para-thyroid hormone, angiopoietin 1, del-1, erythropoietin, fas (CD95), follistatin, macrophage migration inhibitory factor, monocyte chemoattractant protein-1, transferring, and nicotinamide.

The fixation devices of the invention aptly comprise angiogenic precursor material, which is capable of breaking down in vivo to form angiogenic material. Angiogenic precursor materials according to the invention include fibrin, including autologous, allogeneic, xenogeneic, recombinant and synthetic forms thereof, and hyaluronic acid. Degradation fragments of fibrin found to have advantageous angiogenic properties include fragments D and E.

Alternatively, the fixation devices of the invention may comprise tissue-engineered material, which tissue-engineered material is capable of producing angiogenic material. Tissue-engineered material falling within the scope of the invention includes material capable of producing angiogenic material comprising angiogenic factors contained within the first class of angiogenic factors (see above). Tissue-engineered material according to the invention includes, without limitation, proprietary products such as DERMAGRAFT™ and TRANSCYTE™.

Advantageously, the angiogenic material is present in an amount that is therapeutically effective for the mammalian organism in question. Preferably, the angiogenic material is present in an amount that is therapeutically effective for humans. As used herein, the term "therapeutically effective amount" is to be understood to mean sufficient to cause or increase the rate of angiogenesis. What constitutes a therapeutically effective amount is specific to the angiogenic factor(s) comprised within the angiogenic material. In the case of VEGF and FGF-2, for example, the fixation device should comprise up to 50 μg of factor per mg of device, preferably less than 25 μg/mg.

The term "fixation device" includes any devices used to rejoin, re-affix, hold or otherwise partake in the repair of tissue. A non-exhaustive list of such devices includes sutures, surgical arrows, staples, darts, bolts, screws, buttons, anchors, nails, rivets or barbed devices. The fixation devices of the invention also include augmentation devices such as cuffs which are used to promote angiogenisis at the interface of different tissue types such as ligament and bone or tendon and muscle.

Ways of incorporating the angiogenic material into or onto devices according to the invention include the following:

The fixation devices according to the invention may be impregnated with angiogenic material after manufacture of the fixation device. Impregnation may result in angiogenic material being distributed throughout up to the whole of the fixation device. Distribution of the angiogenic material may be homogenous or inhomogenous. In the latter case, the fixation device would comprise localised regions comprising higher concentrations of angiogenic material. Preferably, impregnation results in angiogenic material being present in at least a region extending into the device from at least one of its external surfaces. More preferably, impregnation results in angiogenic material being distributed throughout the whole of the fixation device. Whether the angiogenic material is distributed homogenously or inhomogenously throughout the device and, if inhomogenously, what form the distribution profile has, will depend on the effects to be achieved. In particular, the distribution profile will strongly influence the release profile of angiogenic material into the surrounding tissue.

Impregnation methods, which may be used according to the invention, include, without limitation, dipping, soaking, and under vacuum, if appropriate.

In a second embodiment, the angiogenic factor, material or precursor therefore may be physically incorporated into the main fabric of the fixation device. Aptly, therefore, the angiogenic material will constitute discrete zones within the fabric of the fixation device. Suitably, threads or filaments of angiogenic material may be co-spun or woven together with fibrous or filamentary material comprising the main fabric of the fixation device. For example, threads of angiogenic material may be braided with polyethylene terephthalate or ultra high molecular weight polyethylene fibres used to produce a suture. Alternatively, the angiogenic material may be co-extruded with the main fabric material of the fixation device.

In a third embodiment, the angiogenic material may be coated either directly onto at least one of the external surfaces of the fixation device after manufacture of the fixation device or, alternatively incorporated into a carrier, from which its release can be controlled, and then coated directly onto the fixation device.

Preferably, where the angiogenic factors, materials, or precursors are coated onto or formed as discrete components or zones within the fixation device, they may be first formulated with a hydrophobic polymer to be delivered under controlled release conditions by a diffusion mechanism from the monolithic matrix comprising the factor and hydrophobic polymer. Thus, for example, by incorporating a water miscible or soluble angiogenic material into a polymer matrix, which is hydrophobic in nature, the release rate of the angiogenic material can be controlled. Water is required to solubilise the material, thereby subsequently releasing the material. The degree of hydrophobicity of the polymer matrix controls the rate of water permeation, and hence the rate of release of the angiogenic material.

Preferably, the hydrophobic polymer matrix is polypropylene. Typically, the angiogenic material is blended into the polypropylene forming a mixture which is then drawn into a monofilament. Monofilaments can be twisted or braided to form multifilaments. Preferably, the mixture of angiogenic material and polypropylene monofilaments are co-braided with other polymer fibres or monofilaments, including, without limitation, ultra high molecular weight (UHMW) polyethylene or polyester fibres or monofilaments to form a suture.

Factors which influence the release rate of the angiogenic material include the choice of angiogenic material, the quantity of angiogenic material blended into the polypropylene matrix (also known as the angiogenic factor loading), and the diameter of the monofilaments.

For the purposes of this invention, the hydrophobic polypropylene matrix is used with butyric acid or a butyric acid salt. The salts of butyric acid are inherently stable and have a low volatility. Although the hydrophobic polypropylene matrix may be used with any angiogenic material having appropriate water solubility or miscibility.

Effective use of butyric acid (or salts thereof) as an angiogenic material has not been previously demonstrated. There are two possible reasons for this. The first is that butyric acid has a particularly pungent smell and is unpleasant to use. The second reason is the finding that butyric acid is so rapidly biodegraded that it is unable to effectively promote angiogenesis before it is broken down to ineffective metabolites.

We have found that by formulating butyric acid or water soluble/miscible salts thereof with polypropylene, the noted disadvantages are avoided. The angiogenic material can be delivered at a controlled dosage rate in amounts, which are not malodorous.

Hydroxybutyric acid and derivatives, salts, and polymers thereof, and the butyrin derivatives, such as monobutyrin, may also be formulated with polypropylene.

Thus in accordance with another aspect of the invention there is provided a composition of matter comprising a blend of polypropylene and a water-soluble or water miscible angiogenic material or precursor therefor in a therapeutically effective amount sufficient to promote angiogenisis.

For the purposes of this invention, the composition of matter comprises a blend of polypropylene and butyric acid or a water-soluble or water miscible salt thereof in a therapeutically effective amount sufficient to promote angiogenisis.

Water-soluble or water miscible derivatives of butyric or hydroxy butyric acid, which are suitable for the compositions of matter of the invention, include the sodium, potassium, calcium, ammonium, and lithium salts.

Polypropylene will suitably be admixed or bended with up to about 12% by weight, more suitably up to about 7% by weight, of the angiogenic material.

Polypropylene containing the angiogenic factor can be used as a coating for any fixation device.

The angiogenic material may be coated onto all external surfaces of the fixation device. Coating methods, which may be employed, include dip coating and spray coating.

The present invention further provides a method for the repair of damaged tissue comprising the step of implanting a device in accordance with the invention into a tissue defect.

Preferably, the tissue into which the fixation device is implanted is of minimal vascularity. More preferably, the tissue is meniscal cartilage, articular cartilage, ligament, tendon, bone, or ischaemic tissue. The fixation devices of the invention may be used at the interface of different tissue types, for example between ligament and bone or between muscle and tendon.

The invention will be illustrated by the following Examples.

EXAMPLE 1

O Ti-Cron™ braided sutures, which are non-resorbable and should therefore have no significant effect on angiogenesis, were impregnated with either butyric acid or monobutyrin. The butyric acid impregnated sutures gave a release rate in the range of 25-3000 ng per cm of suture, or 25-3000 ng butyric acid per 1.4 mg of suture per day for 21 days. The sutures were impregnated by soaking them for at least 7 days in a stock solution of butyric acid. The monobutyrin impregnated sutures gave a release rate in the range of 25-3000 ng per cm of suture, or 25-3000 ng monobutyrin per 1.4 mg of suture per day for 7 days. Prior to the surgery the sutures were removed from the stock solution and wiped twice with a surgical swab, Blue Faced Leicester Cross Suffolk Tubs were employed for this example. This is a fairly robust species of sheep with large long bones. Anatomically sheep bones closely approximate to those of man and are regularly used as models for bone graft substitutes and healing. The surgical procedure to implant the suture involved the meniscus being accessed by a standard medial arthrotomy. Using a scalpel, an 8 mm full thickness longitudinal tear was created in the red-white zone of one of the medial menisci.

The tear was then sutured using (i) a 0 Ti-Cron suture which had been impregnated with butyric acid, as detailed above, or (ii) a 0 Ti-Cron suture which had been impregnated with monobutyrin, as detailed above, or (iii) a control untreated 0 Ti-Cron suture which did not contain butyric acid or monobutyrin. The suture technique used was an outside-in horizontal mattress suture. Joints were then closed and the animals allowed to recover.

The animals were permitted to put weight on the joints immediately thereafter and were terminated at the 6 week time point.

FIG. 1 of the accompanying drawings illustrates a tear, which cuts through the red-white zone of meniscal cartilage, made as described supra. FIG. 1 shows a haematoxylin and phloxine stained histological section. The repaired tear is roughly indicated by dotted line (1), which is a red-white tear. The site of the suture location can be seen in the section (3). Angiogenesis (2) in the form of migrating endothelial cells and newly formed blood vessels can be observed as can healing of the tear.

It is the form taken by the angiogenesis which is the best indicator of the success of this experiment: as discussed above, angiogenesis is the formation of new blood vessels from existing ones. This means that angiogenesis could only be observed radiating out from existing blood vessels in the red zone and in fact what is observed is a steady front of new blood vessels (2) advancing from the red zone through the transitional zone towards the white zone.

Figure 2:
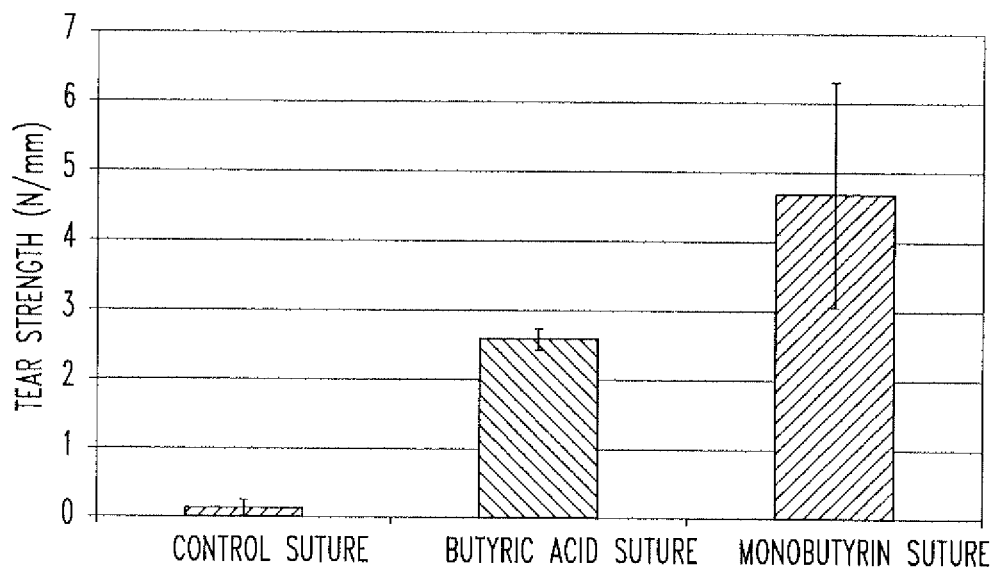
FIG. 2 shows results from biomechanical tests performed on treated menisci.

With reference to FIG. 2, biomechanical evaluation was performed on treated menisci biopsied after 6 weeks in-vivo. The test was based on experiments performed by Roeddecker et al. (1994) which involved circumferentially tearing menisci and measuring average tear loads and average tear energies of the repaired areas.

Initially, an incision of approximately 5-10 mm was made in the posterior horn of each meniscus to produce two "free ends". This incision was positioned to align with, and meet, the repaired area of meniscus. Fully repaired areas of meniscus were sometimes hard to identify, so the incision was positioned according to best judgement. The sutures used to initiate the repair were exposed at the periphery of the meniscus and the suture knots were removed.

Testing was performed using the Instron 5566 materials test machine. The "free ends" of each meniscus were gripped using pincer grips and a 100 N capacity load cell was used to measure the resultant tear load throughout the test. Once complete, the average tear load, from the force/displacement curve, was identified using two cursors and the tear energies under this same area of the force/displacement curves were automatically calculated.

Three control menisci were tested, where the repairs were initiated with untreated suture, three were tested where the suture had been impregnated with butyric acid, and three were tested where the suture had been impregnated with monobutyrin.

The sutures impregnated with an angiogenic factor substantially increased the strength of the repair tissue above that of the untreated control. Normal meniscal tissue has a tear strength of 14 N/mm

EXAMPLE 2

Monofilament Suture

Polypropylene (ECM Plastics) and sodium butyrate (Alfa Aesar, Purity: 99%) were mixed in a Leistritz twin screw extruder. Four mixtures were made, each one containing 2.5, 5, 7.5 and 10% w/w of sodium butyrate. The mixtures were extruded to form rods which were then further processed to form pellets. The pellets were then extruded into USP size 5-0 monofilaments, (USP sizes defined in USP 29, 2006). Pellets formed from the 5% w/w mixture were also extruded into USP size 6-0 monofilaments.

The total sodium butyrate content of the monofilaments was measured by liquid chromatography (HPLC) following extraction in de-ionised water at 90° C. To determine the release rate and total release of sodium butyrate(NaB) from the monofilaments, monofilaments of 20 inch length were placed in phosphate buffered saline (PBS) at 37° C. Analysis of the PBS for the presence of butyrate was carried out by HPLC every day over a period of 28 days. After each analysis, the PBS was replaced with fresh PBS.

Figure 3:
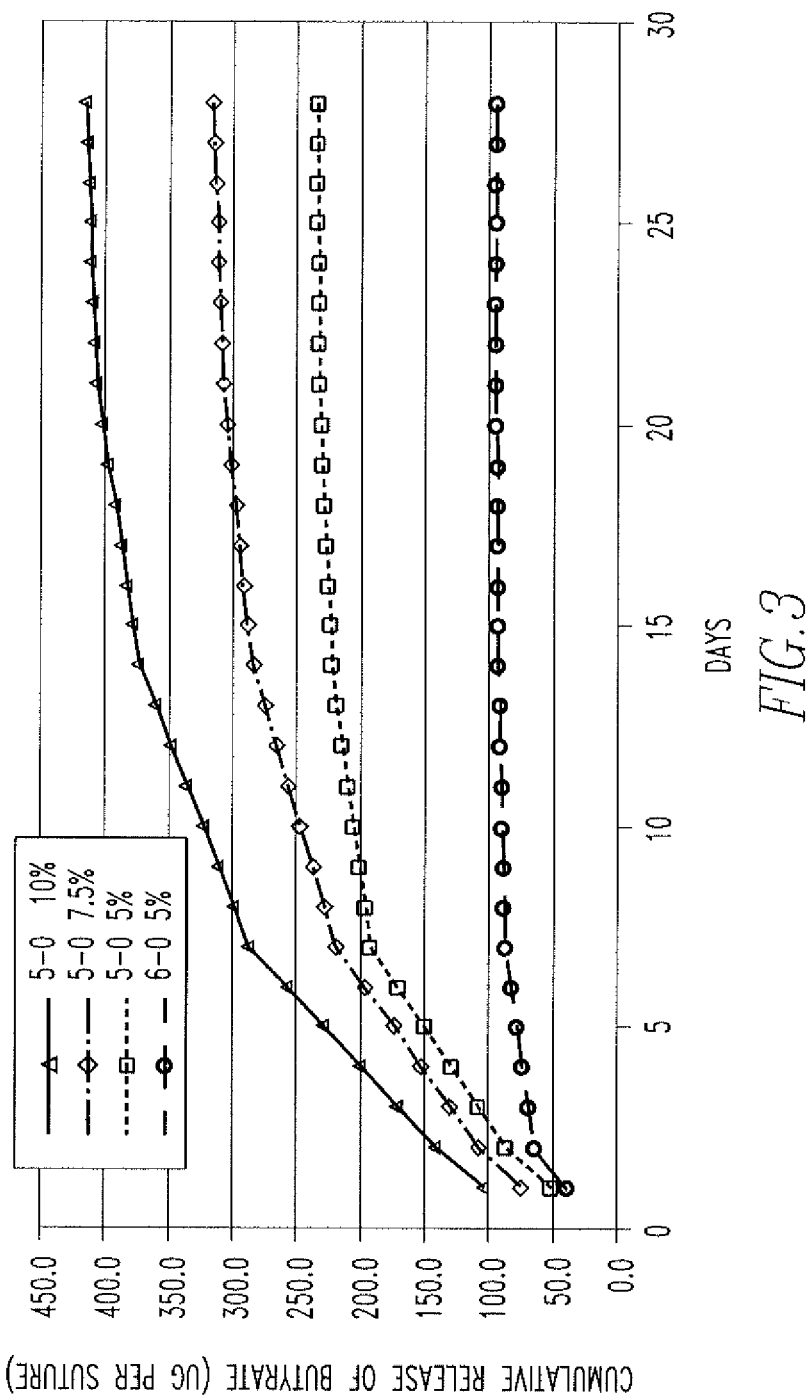
FIG. 3 shows cumulative release rates of butyrate from size 5-0 and size 6-0 monofilaments.

The sodium butyrate content for the 5-0 monofilaments was found to be within the range of 1.9 to 7.5 % w/w. The 6-0 monofilament was found to have a total sodium butyrate content of 4.1% w/w. FIG. 3 illustrates the cumulative release rates from the 5-0 monofilaments. It was found that the release rate of the sodium butyrate from the 5-0 monofilaments depended on both the suture diameter and the initial concentration of the sodium butyrate. In all cases, the release of the sodium butyrate was exhausted after approximately 28 days.

EXAMPLE 3

Braided Suture

Polypropylene (ECM Plastics) and sodium butyrate (Alfa Aesar, Purity: 99%) were mixed in a Leistritz twin screw extruder. Mixtures containing 5 and 7.5% w/w of sodium butyrate were made. The mixtures were extruded to form rods which were then further processed to form pellets. The pellets were then extruded into USP size 5-0 monofilaments and USP size 6-0 monofilaments.

Three end USP size 6-0 monofilaments of 5% w/w sodium butyrate were then braided with ultra high molecular weight polyethylene filaments to form a mixed, sized No. 2 braded suture. A sized No. 0 braided suture was also manufactured using three different monofilament/polyethylene mixes. The three size 0 sutures had either one or two ends of USP size 5-0 monofilaments of 7.5% w/w sodium butyrate, or two ends of USP size 6-0 monofilaments of 5% w/w sodium butyrate braided with ultra high molecular weight polyethylene filaments.

The total sodium butyrate content of the sutures was measured by liquid chromatography (HPLC) following extraction in de-ionised water at 90° C. To determine the release rate and total release of sodium butyrate from the sutures, weighed lengths of each suture were placed in phosphate buffered saline (PBS) at 37° C. Analysis of the PBS for the presence of butyrate was carried out by HPLC over a period of 28 or 56 days. After each analysis, the PBS was replaced with fresh PBS.

Figure 4:
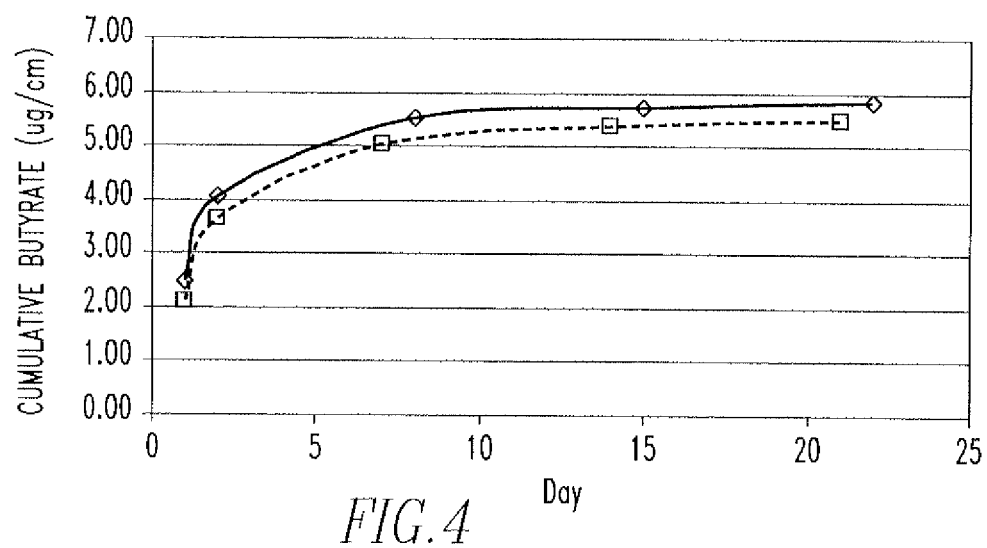
FIG. 4 shows the release rate of butyrate from two different batches of No. 2 suture.

FIG. 4 illustrates the release rate of butyrate from two different batches of the No. 2 suture. The two batches gave similar release rates up to approximately 21 days and demonstrated the consistency of both the manufacture of the suture and the release of the sodium butyrate therefrom.

EXAMPLE 4

Figure 5:
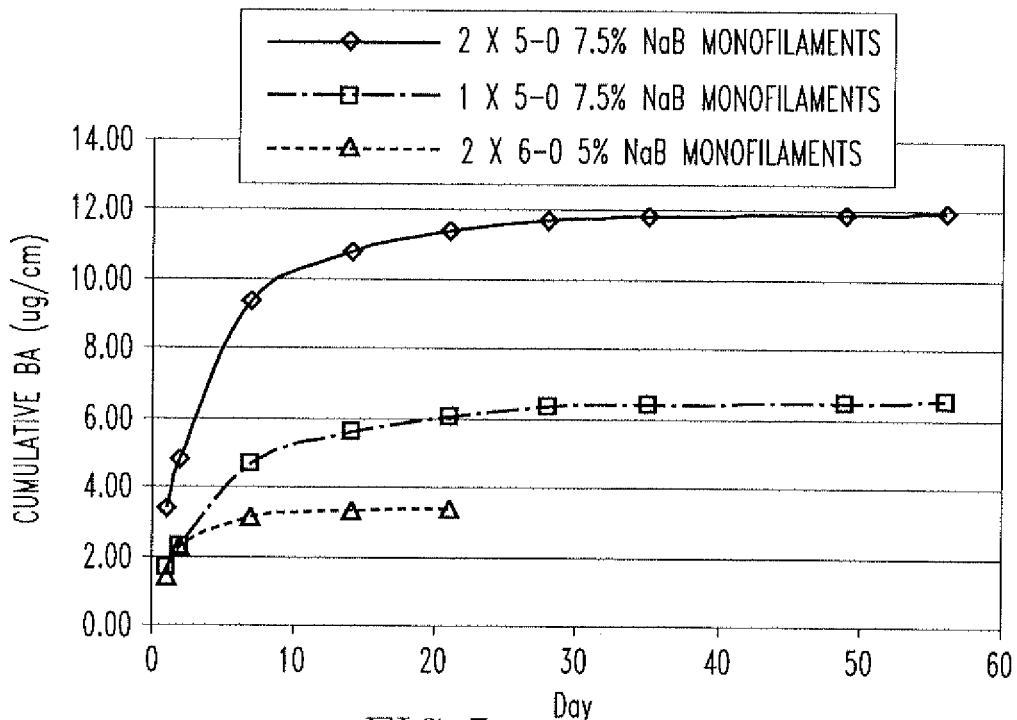
FIG. 5 shows the release rate of sodium butyrate from three different configurations of size No. 0 sutures.

FIG. 5 illustrates the release rate of sodium butyrate from the three configurations of the sized No. 0 sutures of Example 3. The composition, size, and number of the monofilaments within the suture were found to influence both the release rate and total release of the sodium butyrate from the suture.

EXAMPLE 5

Butyric acid and salts thereof were formulated with different polymer compositions and the rate of release into PBS determined.

Figure 6:
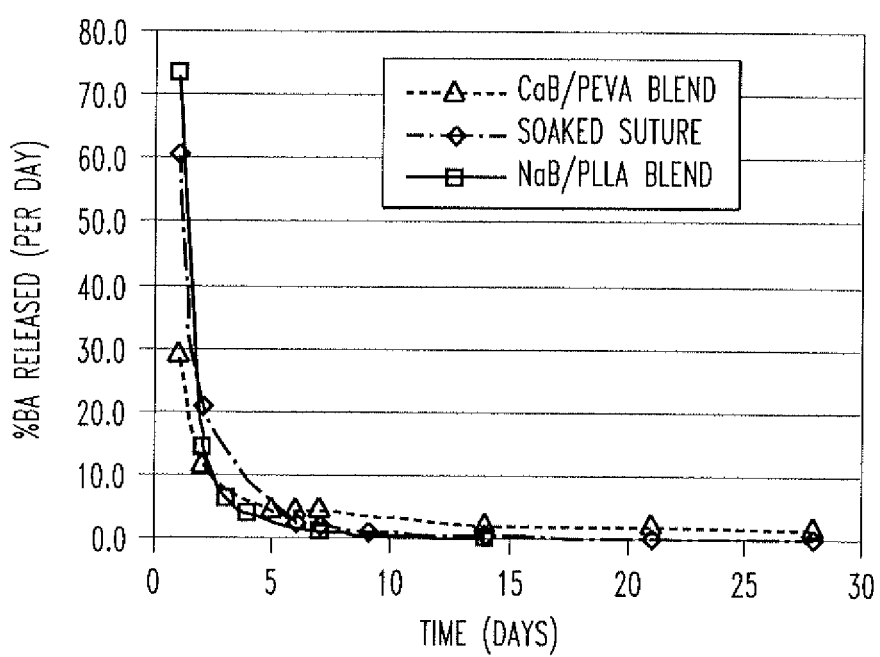
FIG. 6 shows the release rate of butyric acid from different polymer compositions.

Example 5a: Sutures made from 0 Ti-Cron were soaked in solutions of butyric acid (50,000 µg cm$^{-3}$). After 66 h, the sutures were removed from the butyric acid solution and placed in 2 ml of PBS. The PBS was replaced on a daily basis for up to seven days and then at 2 and 3 week timepoints. The isolated PBS extracts were analysed for butyric acid content using an HPLC method. Over 90% of the butyric acid was released within the first four days (FIG. 6).

Example 5b: Sodium butyrate (1% w/w) was compounded into poly (L) lactic acid (PLLA) and then rods of the polymer extruded. The release rate of butyric acid form these rods was evaluated as described above. Butyric acid was released rapidly from the PLLA into PBS (FIG. 6).

Example 5c: Calcium butyrate (1% w/w) was compounded into an ethylene-vinyl acetate copolymer (33% by weight vinyl acetate content) and then rods of the polymer extruded. The release rate of butyric acid from these rods was evaluated as described above. Thus it can be seen that by altering the hydrophobicity of the polymer, the release rate of an angiogenic factor can be controlled (FIG. 6).

EXAMPLE 6

Figure 7A:
FIGS. 7A-7C illustrate a patellar tendon repair procedure on a sheep limb.
Figure 7B:
Figure 7C:
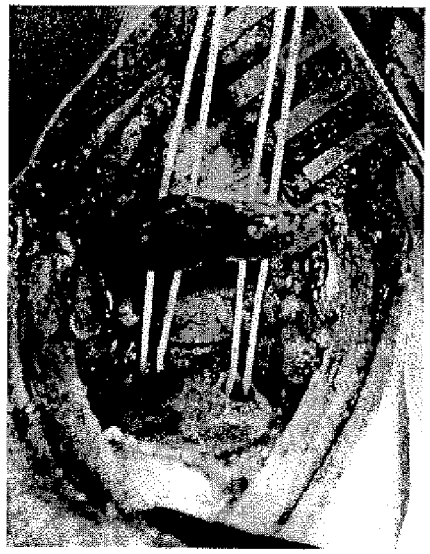

Acute repair in a sheep was performed using the patellar tendon. The surgical protocol used for this repair can be found in Newsham-West R, Nicholson H, Walton M, Milburn P. *Long-term morphology of a healing bone tendon interface: a histological observation in a sheep model*, Journal of Anatomy, Vol. 210, (2007), pp. 318-327, the disclosure of which is incorporated herein by reference in its entirety. Prior to the surgical repair, the sheep knee joint was immobilized in 5°-10° of flexion to prevent tensile loading of the patellar tendon during healing. Once the joint was immobilized, the tendon was pared off the tibial bone with a scalpel blade. The exposed bone surface was scraped clean of any remaining tendon and then gently ground with a dental bur until there was a slight vascular blush. Two holes were then made in the tibial bone via the use of a drill. The prepared bone bed is shown in FIG. 7A. As shown in FIG. 7B, two suture anchors were then implanted into the holes of the prepared bone bed. The anchor sutures were then passed vertically through the tendon, as shown in FIG. 7C, and the sutures were tied in order to secure the tendon onto the bone surface. External fixation was applied to the surgical area and knee immobilization was maintained for 3 weeks post-surgery, After 3 weeks, the external fixation was removed and the animals were allowed to return to full weight bearing. The sutures used in the anchors were braided sutures made from monofilaments that had been extruded from polypropylene compounded with sodium butyrate. Prior to the repair, the braided suture material was tested for total sodium butyrate content and butyric acid release over time. All samples were tested in quadruplicate. Finished test suture was found to contain on average 7.4 µg/cm sodium butyrate (range of 6.6-9.0 µg/cm) and butyric acid release from the suture was detectable for 28 days in vitro, thereby demonstrating an extended release.

A second identical repair was done with suture anchors that included suture made from polypropylene monofilaments that had been extruded only from polypropylene and had not been compounded with sodium butyrate. This suture was used as a control.

Figure 8:
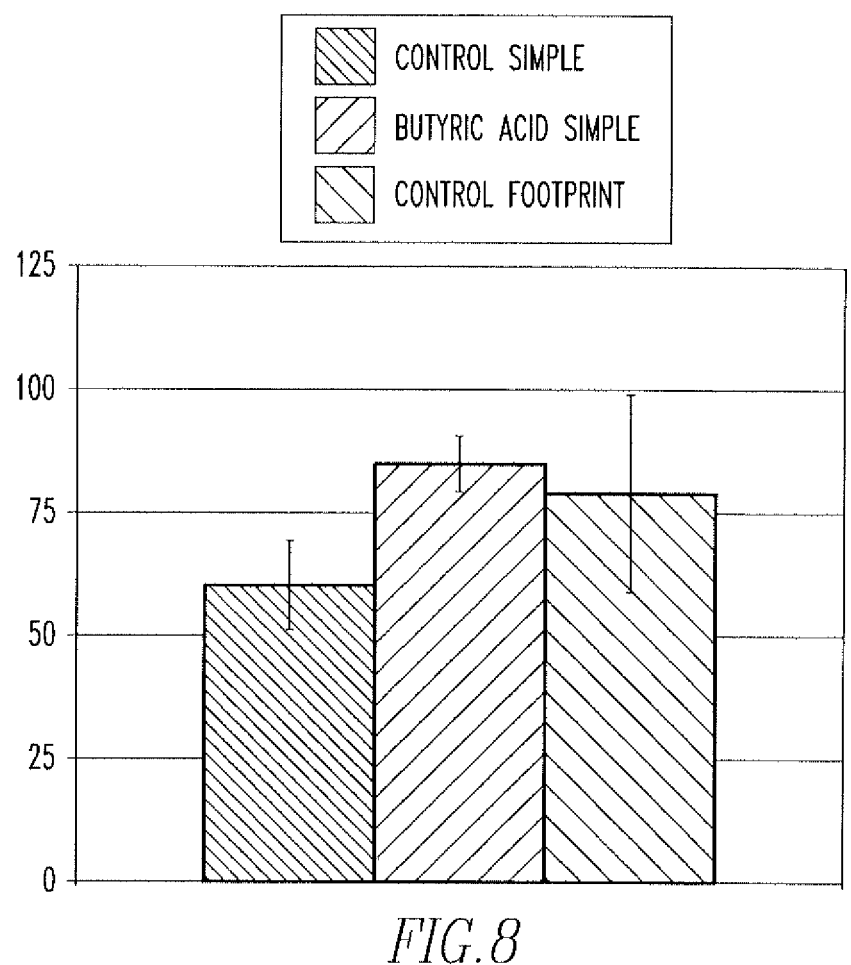
FIG. 8 shows the mechanical testing results of tendon healing after the repair shown in FIGS. 7A-7C.

After 12 weeks, mechanical testing of tendon healing was performed. The testing demonstrated that the use of a butyric acid containing suture in a simple suture configuration repair lead to a statistically significant (p<0.01) enhancement (41%) of the strength to failure properties of the repaired bone to tendon interface when compared to the control suture in the same simple configuration. It was observed that the enhancement in strength to failure with butyric acid containing sutures was similar to repairs using a more complex footprint suture configuration. As shown in FIG. 8, there was a 41% increase with butyric acid and a 31% increase with modified footprint suture configuration compared to the simple configuration with the control suture.

Figure 9A:
FIGS. 9A and 9B illustrate control and butyric acid containing suture repaired tendon-bone interfaces.
Figure 9B:
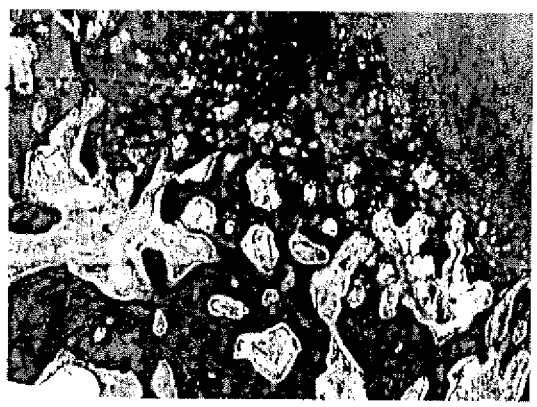

Histologically, the control and butyric acid containing suture repaired tendon-bone interfaces look similar with some evidence of increased osteogenic activity in the butyric acid suture samples. FIG. 9A represents the control suture repaired tendon-bone interface and FIG. 9B represents the butyric acid containing suture repaired tendon-bone interface. The dotted lines in FIGS. 9A and 9B represent the bone to tendon interface.

In conclusion, the butyric acid containing suture enhanced tendon to bone healing, when compared to the control suture, as measured by mechanical testing of the strength to failure of the tendon-bone interface after twelve weeks of healing in an acute model of tendon repair in a sheep. This data supports the conclusion that the use of a pro-angiogenic suture represents a viable approach for improving tendon to bone healing.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A suture for repair of a tissue tear comprising three end USP size 6-0 polypropylene monofilaments intertwined with ultra-high molecular weight polyethylene filaments, wherein the polypropylene monofilaments comprises an angiogenic material in admixture with the polypropylene, wherein the angiogenic material is sodium butyrate and the monofilaments comprise 5% w/w of the sodium butyrate.

2. The suture of claim 1, having the angiogenic precursor material impregnated into at least one region thereof.

3. The suture of claim 1 wherein the suture is a sized No. 2 suture.

4. The suture for repair of a tissue tear according to claim 1, wherein upon placement of the suture within a mammalian organism, complete release of the sodium butyrate from the suture occurs within about 28 days.

5. The suture for repair of a tissue tear according to claim 1 wherein the ultra-high molecular weight polyethylene filaments comprise monofilaments.

6. The suture for repair of a tissue tear according to claim 1 wherein the ultra-high molecular weight polyethylene filaments comprise multifilaments.

7. The suture for repair of a tissue tear according to claim 1 wherein the polypropylene monofilaments are co-braided with the ultra-high molecular weight polyethylene filaments.

* * * * *